United States Patent
Bharat et al.

(10) Patent No.: US 10,376,714 B2
(45) Date of Patent: Aug. 13, 2019

(54) METHOD FOR IMPROVED SURFACE TRACKING-BASED MOTION MANAGEMENT AND DYNAMIC PLANNING IN ADAPTIVE EXTERNAL BEAM RADIATION THERAPY

(71) Applicant: KONINKLIJKE PHILIPS N.V., Eindhoven (NL)

(72) Inventors: Shyam Bharat, Cortlandt Manor, NY (US); Kongkuo Lu, Briarcliff Manor, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 749 days.

(21) Appl. No.: 14/772,805

(22) PCT Filed: Mar. 17, 2014

(86) PCT No.: PCT/IB2014/059884
§ 371 (c)(1),
(2) Date: Sep. 4, 2015

(87) PCT Pub. No.: WO2014/155232
PCT Pub. Date: Oct. 2, 2014

(65) Prior Publication Data
US 2016/0016007 A1 Jan. 21, 2016

Related U.S. Application Data

(60) Provisional application No. 61/804,827, filed on Mar. 25, 2013.

(51) Int. Cl.
*A61N 5/10* (2006.01)
*A61B 6/00* (2006.01)

(52) U.S. Cl.
CPC .......... *A61N 5/1037* (2013.01); *A61N 5/107* (2013.01); *A61N 5/1039* (2013.01);
(Continued)

(58) Field of Classification Search
CPC .... A61N 5/103; A61N 5/1037; A61N 5/1038; A61N 5/1039; A61N 5/1049;
(Continued)

(56) References Cited

U.S. PATENT DOCUMENTS

| 6,298,260 B1 | 10/2001 | Sontag et al. |
| 7,596,207 B2 | 9/2009 | Kaus |

(Continued)

FOREIGN PATENT DOCUMENTS

| EP | 2 292 300 A1 | 3/2011 |
| WO | 2010109345 A1 | 9/2010 |

*Primary Examiner* — Carrie R Dorna

(57) ABSTRACT

A therapy system and method treats an internal target of a patient (16). A treatment plan (36) is received to treat the internal target. The treatment plan (36) includes a plurality of treatment fractions including correspondences (38) between the internal target and an external body surface based on a pre-procedural planning image (14) and pre-procedural tracking data (20). Before selected treatment fractions of the plurality of treatment fractions, a pre-fraction planning image (50) of the target is received, tracking data (20, 52) of the external body surface of the patient (16) is received, and the correspondences (38) between the internal target and the external body surface are updated based on the received pre-fraction planning image (50) and the received tracking data (20, 52). Therapy is delivered to the patient (16) in accordance with the treatment plan (36) and using the updated correspondences (38).

18 Claims, 3 Drawing Sheets

(52) U.S. Cl.
CPC ......... *A61N 5/1049* (2013.01); *A61N 5/1068* (2013.01); *A61B 6/5264* (2013.01)

(58) Field of Classification Search
CPC .. A61N 5/1064; A61N 5/1068; A61N 5/1069; A61N 5/107; A61B 6/5264; A61B 6/527; A61B 6/5288
See application file for complete search history.

(56) References Cited

U.S. PATENT DOCUMENTS

| | | |
|---|---|---|
| 7,693,257 B2 | 4/2010 | Allison |
| 7,708,682 B2 | 5/2010 | Pekar et al. |
| 8,130,384 B2 | 3/2012 | Kindlein et al. |
| 2007/0015991 A1* | 1/2007 | Fu .......................... A61B 8/08 600/407 |
| 2007/0286331 A1 | 12/2007 | Keall et al. |
| 2010/0208274 A1* | 8/2010 | Kindlein ................. A61B 6/08 356/603 |
| 2012/0002780 A1 | 1/2012 | Forthmann et al. |
| 2012/0008735 A1 | 1/2012 | Maurer et al. |
| 2012/0226152 A1 | 9/2012 | Porikli |

\* cited by examiner

METHOD FOR IMPROVED SURFACE TRACKING-BASED MOTION MANAGEMENT AND DYNAMIC PLANNING IN ADAPTIVE EXTERNAL BEAM RADIATION THERAPY

CROSS REFERENCE TO RELATED APPLICATIONS

This application is a national filing of PCT application Serial No. PC/IB2014/059884, filed Mar. 17, 2014, published as WO 2014/155232 A1 on Oct. 2, 2014, which claims the benefit of U.S. provisional application Ser. No. 61/804,827 filed Mar. 25, 2013, which is incorporated herein by reference.

The present application relates generally to external beam radiation therapy (EBRT). It finds particular application in conjunction with surface tracking-based motion management and dynamic planning, and will be described with particular reference thereto. However, it is to be understood that it also finds application in other usage scenarios and is not necessarily limited to the aforementioned application.

EBRT is delivered over multiple fractions spread over many weeks, but is usually designed based on a single static treatment plan. Failure to take in to account intrafraction motion (e.g., respiratory motion, cardiac motion, etc.) and interfraction motion (e.g., tumor shrinkage due to progressive radiation damage) can result in incomplete dose coverage of targets (e.g., tumors) and damage to surrounding normal tissue, which can include organs at risk (OARs). To ensure complete coverage of targets, margins are usually added around the target. These margins are usually static and large enough to cover the entire range of motion of the target. However, margins can increase damage to surrounding normal tissue, especially during certain phases of the respiratory cycle. Tumors can shrink during the course of fractions, thus, exacerbating the damage to surrounding normal tissue and bringing it into the "hot spots" of treatment beams, if the treatment beams are not appropriately adjusted.

To address the problems of intrafraction and interfraction motion, dynamic planning target volume (PTV) margins and delivery gating have been proposed. PTV margins are dynamically adjusted by changing the PTV contours based on gathered real-time motion data and target motion prediction models. For example, the path of the target is followed by changing the positions of multi-leaf collimator (MLC) leaves on a linear particle accelerator (LINAC). Delivery gating utilizes gathered real-time motion data of the target captured during treatment delivery to determine whether treatment beams need to be turned on or off. Approaches to quantifying real-time motion include wireless electromagnetic (EM) transponders, on-board imaging (e.g., magnetic resonance imaging (MRI) and ultrasound (US)), body surface tracking, etc. Body surface tracking (e.g., using high speed cameras) is inexpensive and easy to implement for real-time motion quantification. To make use of surface motion data, however, the correspondence between body surface motion and internal target motion needs to be known accurately.

Body surface tracking has previously been proposed in combination with anatomical data from a pre-procedural four-dimensional (4D) computed tomography (CT) image to predict target motion patterns. Using body surface tracking in this way, the correspondence between external body shape and internal target shape is defined for each phase of the respiratory cycle. Therefore, given a particular body surface shape detected at any time during treatment delivery, the internal target shape and position can be predicted. The accuracy of the predication relies upon repeatability in the manifestation of breathing on internal organ motion. The prediction can be used to implement delivery gating schemes or to implement dynamic PTV margins, whereby surrounding normal tissue and OARs are at less risk to radiation exposure.

Challenges with the foregoing approach to predicting target motion patterns include the foregoing approach's inability to quantify patient-specific tumor shape and size changes that occur during the course of radiation. Tumor shrinkage is a common occurrence during radiation therapy, especially during the middle-to-latter fractions. In fact, radiation therapy is often used to shrink tumors prior to surgical removal. Furthermore, during treatment, there might be slight changes in respiratory pattern that vary the correlation between external body shape and internal target shape over time. Registration errors will then accumulate during treatment, resulting in incorrect prediction of target motion for treatment delivery. Therefore, designing delivery gating schemes and dynamic treatment plans based on the original size and shape of the tumor is not only inefficient but also leads to harmful dosing of surrounding normal tissue.

The present application provides a new and improved system and method which overcome the above-referenced problems and others.

In accordance with one aspect, a therapy system for treating an internal target of a patient is provided. The therapy system includes at least one processor programmed to receive a treatment plan to treat the internal target. The treatment plan includes a plurality of treatment fractions including correspondences between the internal target and an external body surface based on a pre-procedural planning image and pre-procedural tracking data. The at least one processor is further programmed to, before selected treatment fractions of the plurality of treatment fractions, receive a pre-fraction planning image of the target, receive tracking data of the external body surface of the patient, and update the correspondences between the internal target and the external body surface based on the received pre-fraction planning image and the received tracking data. That at least one processor is also programmed to provide the treatment plan and the updated correspondences to a therapy delivery system configured to deliver therapy to the patient in accordance with the treatment plan and using the updated correspondences.

In accordance with another aspect, a therapy method for treating an internal target of a patient is provided. A treatment plan to treat the internal target is received. The treatment plan includes a plurality of treatment fractions including correspondences between the internal target and an external body surface based on a pre-procedural planning image and pre-procedural tracking data. Before selected treatment fractions of the plurality of treatment fractions, a pre-fraction planning image of the target is received, tracking data of the external body surface of the patient is received, and the correspondences between the internal target and the external body surface are updated based on the received pre-fraction planning image and the received tracking data. The treatment plan and the updated correspondences are provided to a therapy delivery system configured to deliver therapy to the patient in accordance with the treatment plan and using the updated correspondences.

In accordance with another aspect, a therapy delivery system for treating an internal target of a patient is provided.

The therapy system includes a planning system configured to generate a treatment plan to treat the internal target. The treatment plan includes a plurality of treatment fractions. The therapy system further includes a synchronization module configured to, before each of one or more treatment fractions selected from the plurality of treatment fractions, update a size and shape of the internal target and update the treatment plan for the updated target size and shape. The planning system is configured to provide the updated treatment plan to a delivery control system configured to deliver therapy to the patient in accordance with the updated treatment plan.

One advantage resides in taking in to account tumor shrinkage when predicting target motion patterns.

Another advantage resides in reduced dose to normal tissue, which can include organs at risk (OARs) surrounding targets.

Another advantage resides in more complete dosing of targets.

Another advantage resides in improved tracking of target and OAR motion.

Another advantage resides in reduced planning target volume (PTV) margins.

Another advantage resides in improved delivery gating.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
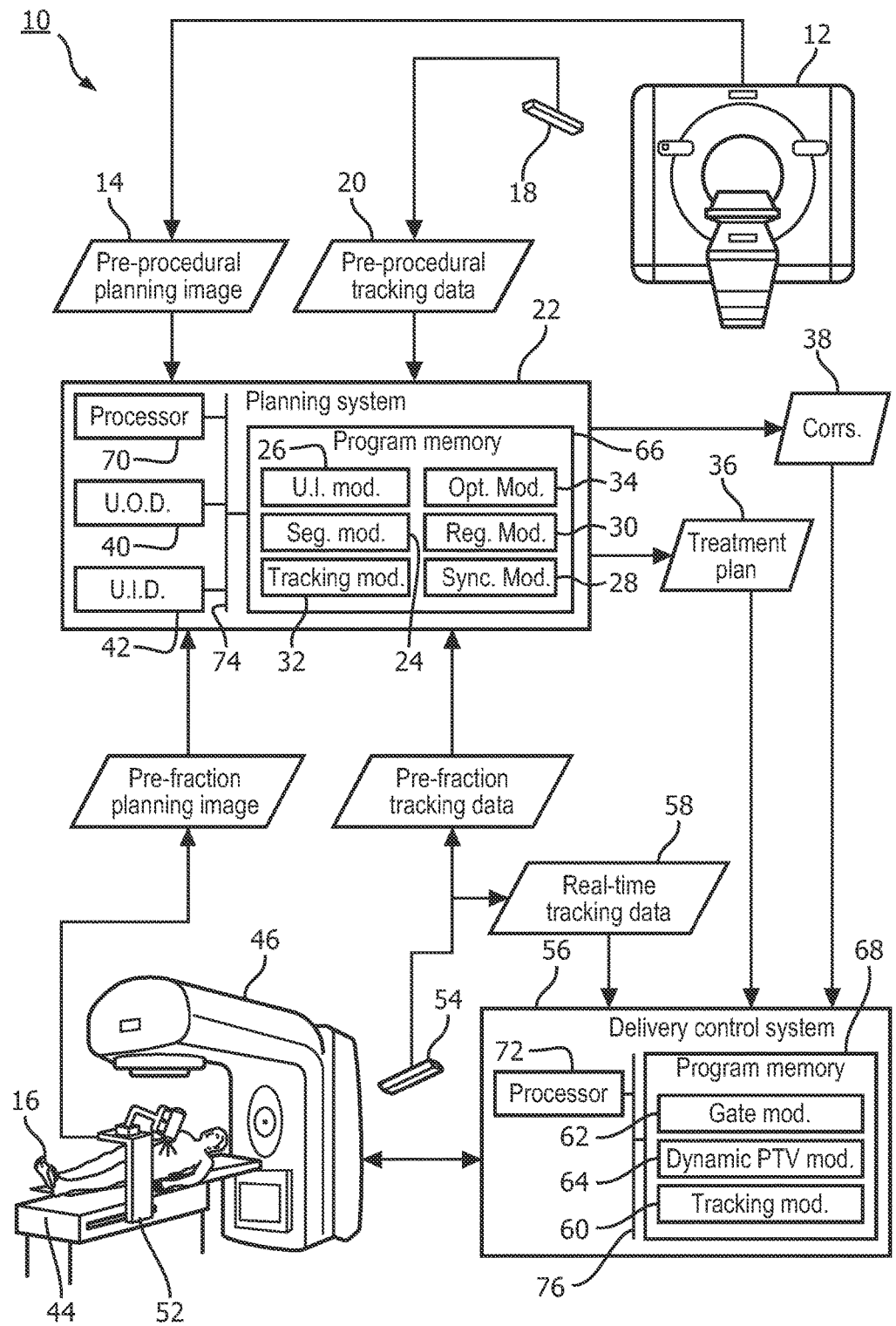
FIG. 1 illustrates a therapy system using body surface tracking for improved therapy delivery.

With reference to FIG. 1, a therapy system 10 (e.g., an external beam radiation therapy (EBRT) system) includes a pre-procedural imaging system 12, which generates a pre-procedural planning image 14 of a target of a patient 16, and normal tissue of the patient 16 surrounding the target. The surrounding normal tissue commonly includes one or more organs at risk (OARs), and the target is commonly a lesion, such as a tumor, to be treated. Further, the pre-procedural planning image 14 can include the external body surface of the patient 16 adjacent the target. For example, where the target is a tumor in a lung of the patient 16, the external body surface is the external chest surface of the patient 16.

The pre-procedural planning image 14 is typically four-dimensional (4D), whereby it typically includes a three-dimensional (3D) image for each of a plurality of time points. This is to be contrasted with a 3D image which only includes a single time point. The plurality of time points can, for example, correspond to the phases of a motion cycle of the patient 16 (e.g., the respiratory cycle of the patient) and suitably span multiple motion cycles. The pre-procedural planning image 14 can be generated using any imaging modality but is suitably generated using one of computed tomography (CT), positron emission tomography (PET), magnetic resonance (MR), single photon emission computed tomography (SPECT), ultrasound (US), cone-beam computed tomography (CBCT), and the like.

A pre-procedural tracking system 18 of the therapy system 10 measures the external body surface of the patient 16, which can be included in the pre-procedural planning image 14, during the generation of the pre-procedural planning image 14 to generate pre-procedural tracking data 20. The pre-procedural tracking data 20 includes a sample measurement of the external body surface (e.g., size, shape, contours, etc.) of the patient 16 at time points of the pre-procedural planning image 14. Typically, the pre-procedural tracking system 18 uses one or more high speed cameras to generate the pre-procedural tracking data 20. However, other approaches to generating the pre-procedural tracking data 20 are also contemplated.

A planning system 22 of the therapy system 10 receives the pre-procedural planning image 14 (e.g., a 4D CT image) from the pre-procedural imaging system 12 and the pre-procedural tracking data 20 (e.g., a 4D image of the external body surface of the patient 16) from the pre-procedural tracking system 18. The pre-procedural planning image 14 and the pre-procedural tracking data 18 are applied to a plurality of modules of the planning system 22, including a segmentation module 24, a user interface module 26, a synchronization module 28, a registration module 30, a body surface tracking module 32, and an optimization module 34, to generate a treatment plan 36, and correspondences 38 between the external body surface and the target, for the patient 16.

The segmentation module 24 receives an image (e.g., the pre-procedural planning image 14) and delineates one or more regions of interest (ROIs) in the image, such as a target and/or OARs. The ROIs are typically delineated with contours tracing the boundaries of the ROIs in the image. Delineation can be performed automatically and/or manually. As to automatic delineation, any number of known segmentation algorithms can be employed. As to manual delineation, the segmentation module 24 cooperates with the user interface module 26 to allow clinicians to manually delineate the regions in the image and/or manually adjust automatic delineations of the regions in the image.

The user interface module 26 presents a user interface to an associated user with a user output device 40 (e.g., a display) of the planning system 22. The user interface can allow the user to at least one of delineate ROIs in an image, modify delineations of ROIs in an image, and view delineations of ROIs in an image. Typically, the user delineates a ROI of an image by drawing a contour along the boundary of the ROI on the image using a user input device 42 (e.g., a computer mouse) of the planning system 22. Further, a delineation of a ROI in an image is typically viewed by overlaying a representative contour on the image and modified by resizing and/or reshaping the representative contour using the user input device 42. The user interface can also allow the user to enter and/or define parameters for generating and/or updating a treatment plan using the user input device 42.

The synchronization module 28 receives a first anatomical data set of a patient (e.g., the pre-procedural planning image 14) and a second anatomical data set of the patient (e.g., the pre-procedural tracking data 20), each data set including one or more time points. Based on the first and second data sets, the synchronization module aligns the time points of the first data set with the time points of the second data set based on phase in a motion cycle (e.g., respiratory cycle) of the patient.

The synchronization can be performed by direct analysis of the first and second data sets. For example, the motion cycle can be extracted for each of the first and second data sets from analysis (e.g., image analysis) of features of the first and second data sets. The extracted motion cycles can then be aligned and used to align the time points of the first and second data sets. As another example, the first and second data sets can be matched (e.g., using image matching) to determine a best alignment of the time points of the first and second data sets. The synchronization can also be performed by analysis of metadata of the first and second data sets. For example, each time point in the first and second data sets can be annotated with cardiac or respiratory phase, whereby cardiac or respiratory phase in the metadata is used for alignment of the time points of the first and second data sets. As another example, each time point in the first and second data sets can be annotated with a time stamp, whereby time in the metadata is used to perform alignment of the time points of the first and second data sets. The synchronization can also be performed by a combination of the foregoing approaches or any other approach to synchronizing.

The registration module 30 translates a first anatomical data set within a first coordinate frame (e.g., the pre-procedural tracking data 20) to a second coordinate frame of a second anatomical data set (e.g., the pre-procedural planning image 14). Any number of well-known registration algorithms can be employed with anatomical features or artificial features shared by the first and second data sets. For example, the first data set can be deformably registered to the second data set using a deformable image registration (DIR) algorithm with anatomical features shared by the first and second data sets. As another example, the first data set can be registered to the second data set using fiducial markers implanted with the patient 16 and common to both the first and second data sets. Fiducial markers are ideal where anatomical features are difficult to find on both data sets due to, for example, changes in anatomy because of EBRT or disease progression. As another example, the first data set can be registered to the second data set using segmented structures in the first and second data sets.

When the first and second data sets are 4D, the registration includes synchronizing the first and second data sets. In some instances, this includes synchronizing the first and second data sets using the synchronization module 28. A 4D registration algorithm can then be applied to register the first synchronized data set with the second synchronized data set, or a 3D registration algorithm can then be applied, for each pair of aligned time points, to register data in the first synchronized data set corresponding to the first time point of the pair to data in the second synchronized data set corresponding to the second time point of the pair. Alternatively, a 4D registration algorithm can be applied to register the first data set with the second data set without first synchronizing the first and second data sets using the synchronization module 28, thereby synchronizing the first and second data sets. For example, the 4D registration algorithm can find the best spatial matches between time points of the first and second data sets.

The body surface tracking module 32 receives an anatomical image (e.g., the pre-procedural planning image 14) including a target, normal tissue surrounding the target and, typically, an external body surface adjacent the target. Further, the body surface tracking module 32 receives a delineation of the target in the anatomical image. Alternatively, the delineation of the target in the anatomical image is determined using the segmentation module 24. Even more, the body surface module 32 receives tracking data (e.g., the pre-procedural tracking data 20) describing the external body surface. The tracking data can be: 1) tracking data describing the external body surface during the generation of the anatomical image; 2) tracking data describing the external body surface during the generation of another anatomical image sharing common ROIs (e.g., the target) with the anatomical image and synchronized with the other anatomical image; or 3) other tracking data describing the external body surface.

The anatomical image is typically a collection of 3D images (i.e., a 4D image) collected over a period of time, such as a plurality of respiratory cycles. When the anatomical image is 4D, the tracking data is a collection of sample measurements collected over the period of time or another period of time of similar in length as the period of time. For example, where the anatomical image is collected over a plurality of respiratory cycles, the tracking data is collected over a plurality of respiratory cycles, which need not be the same as the plurality of respiratory cycles of the anatomical image.

Further, when the anatomical image is 4D, the body surface tracking module 32 synchronizes and registers the anatomical image with the tracking data using the registration module 30. Typically, this is performed by registering the tracking data to the anatomical image, or vice versa, to bring the anatomical image and the tracking data into a common coordinate frame. However, other approaches are contemplated. For example, this can alternatively be performed by registering both the anatomical image and the tracking data to another anatomical image or other tracking data using the registration module 30.

When the tracking data corresponds to the anatomical image, the registration module 30 can be used to synchronize the anatomical image and the tracking data using, for example, time stamps. When the tracking data describes the external body surface during the generation of another anatomical image sharing common ROIs with the anatomical image and is synchronized with the other anatomical image, the registration module 30 can synchronize the anatomical image with the tracking data by registering or synchronizing the anatomical image to the other anatomical image. When nothing is known about the tracking data other than it describes the external body surface, registration module 30 can synchronize the anatomical image using any suitable approach.

After registration and synchronization, correspondences between the external body surface in the tracking data and the target delineation in the anatomical image are determined by the body surface tracking module 32. For each aligned pair of time points of the anatomical image and the tracking data, correspondences between the external body surface and the target delineation are determined to create, for example, a distance vector, each element of the distance vector corresponding to the distance between a pair of points, one for the delineated target and one for the external body surface. In some instances the correspondences (e.g., the distance vectors) are all combined. Alternatively, the correspondences (e.g., the distance vectors) can be grouped based on motion phase (e.g., respiratory phase) and combined within the groups. Correspondences can be combined by, for example, averaging.

In addition to determining correspondences, the body surface tracking module 32 can extract a motion pattern (i.e., one or more motion cycles) from the tracking data when the tracking data is collected over a period of time. For example, a respiratory pattern can be extracted when the tracking data described the external chest surface of a patient and the tracking data is collected over a period of time. Suitably, the tracking data is first registered and synchronized before extracting the motion pattern.

The optimization module 34 receives input data including: 1) plan parameters for generating a treatment plan for a patient from, for example, the user interface module 26; 2) delineations of a target and, in some instances, surrounding OARs in a planning image of the patient from, for example, the segmentation module 24; 3) typically a motion pattern of the patient (e.g., a respiratory pattern describing one or more respiratory cycles when the target resides in the chest of the patient); and 4) other relevant inputs, such as a delivered dose distribution indicating dose delivered to the target. When the planning image is 4D, the delineations of the target and/or the OARs define motion patterns for the target and/or the OARs.

Based on the received input data, the optimization module 34 generates and/or updates a treatment plan to comply with the plan parameters. The treatment plan can include a planning target volume (PTV), including margins around the target, and a plurality of fractions, each fraction specifying beam directions and beam energies. Alternatively, the treatment plan can include a plurality of PTVs, each including different margins around the target, and a plurality of fractions, each fraction specifying beam directions and energies for irradiating the PTV. The plurality of PTVs suitably correspond to different motion phases (e.g., respiratory phases when the target resides in the chest of the patient). In some instances, PTV location is fixed; whereas, in other instances, PTV location is dynamic based on the location of the target and/or the motion cycle.

To apply the pre-procedural planning image 14 and the pre-procedural tracking data 20 to the modules of the planning system 22, and generate the treatment plan 36 and the correspondences 38, the pre-procedural planning image 14 is segmented to delineate the target and, where applicable, the OARs in the pre-procedural planning image 14 using the segmentation module 24. The optimization module 34 is then provided: 1) the delineations of the target and, where applicable, the OARs; 2) plan parameters (e.g., from the user interface module 26); and 3) typically a motion pattern of the patient 14 (e.g., the respiratory pattern of the patient). The motion pattern can be determined from the pre-procedural tracking data 20 using, for example, the body surface tracking module 32. Based on these inputs, the optimization module 34 generates the treatment plan 36.

In addition to generating the treatment plan 36, correspondences between the external body surface and the target are determined using the body surface tracking module 32. Registration between the pre-procedural planning image 14 and the pre-procedural tracking data 20 can be readily performed anatomical features of the external body surface when the pre-procedural planning image 14 includes the external body surface of the pre-procedural tracking data 20.

At a scheduled day and time for each treatment fraction of the treatment plan 36, the patient 16 is set-up on a treatment couch 44 of a therapy delivery apparatus 46 of the therapy system 10. For select treatment fractions of the treatment plan 36, the treatment plan 36 and the correspondences 38 are updated before carrying out the treatment fraction while the patient 16 is on the treatment couch 44. For example, the updating can be performed for each treatment fraction. As another example, the updating can be performed every predetermined number of treatment fraction, such as every other treatment fraction, or every predetermined period of time, such as once every week. In some instances, the updating is always performed for the first treatment fraction.

To perform the updating for a treatment fraction, a pre-fraction imaging system 48 generates a pre-fraction planning image 50 of the target of the patient 16, and the normal tissue of the patient 16 surrounding the target. The pre-fraction planning image 50 can further include the external body surface of the patient 16 included in the pre-procedural planning image 14. The dimensions of the pre-fraction planning image 50 are equal to the dimensions of the pre-procedural planning image 14. For example, if the pre-procedural planning image 14 is 4D, the pre-fraction planning image 50 is 4D. Further, the time points of the pre-fraction planning image 50 are suitably captured to align with the time points of the pre-procedural image 14. For example, where the time points of the pre-procedural image 14 correspond to the phases of the respiratory cycle of the patient 16, the time points of the pre-fraction image 50 correspond to the phases of the respiratory cycle of the patient 16. The pre-fraction planning image 50 can be generated using any imaging modality but is suitably generated using one of CT, PET, US, MR, SPECT, CBCT, and the like. Due to its small size and ready deployment in conjunction with a patient positioned in a linear particle accelerator (LINAC) or other EBRT system, US is particularly advantageous.

In some instances, pre-fraction tracking data 52 is generated by a delivery tracking system 54 of the therapy system 10 during the generation of the pre-fraction planning image 50. The pre-fraction tracking data 52 includes a sample measurement of the external body surface at time points of the pre-fraction planning image 50. The delivery tracking system 54 typically measures the external body surface of the patient 16 using one or more high speed cameras. However, other approaches to generating the tracking data are contemplated.

The planning system 22 receives the pre-fraction planning image 50 (e.g., a 4D US image) from the pre-fraction imaging system 48 and, in some instances, the pre-fraction tracking data 52 (e.g., a 4D image of the body surface of the patient 16) from the delivery tracking system 54. The target and, where applicable, the OARs are delineated in the pre-fraction planning image 50 using the segmentation module 24.

To expedite segmentation, the delineations in the pre-fraction planning image 50 can be based off the delineations in the pre-procedural planning image 14. For example, the pre-fraction planning image 50 is registered to the pre-procedural planning image 14, or vice versa, using the registration module 30. This allows the delineations in the pre-procedural planning image 14 to be translated in to the coordinate frame of the pre-fraction planning image 50, or vice versa. As another example, the delineations in the pre-procedural planning image 14 are translated in to the coordinate frame of the pre-fraction planning image of the first treatment fraction of the treatment plan 36. Thereafter, pre-fraction planning images of subsequent treatment fractions of the treatment plan 36 are translated to the coordinate frame of the pre-fraction planning image of the first treatment fraction to use the translated delineations.

After segmenting the pre-fraction planning image 50, the optimization module 34 is provided with: 1) delineations of the target and, where applicable, the OARs in the pre-fraction planning image 50; 2) plan parameters; and 3) typically a motion pattern of the patient 14. The motion pattern can be based off the pre-fraction tracking data 52 or some other external data. Based on these inputs, the optimization module 34 updates the treatment plan 36 by re-optimizing one or more of treatment beam directions, the one or more PTVs, and other parameters of the treatment plan 36.

In addition to updating the treatment plan 36, the correspondences between the external body surface and the target are updated using the body surface tracking module 32. The updating uses the pre-fraction planning image 50, and typically the pre-fraction tracking data 52 or the pre-procedural tracking data 20. It includes registering and synchronizing the pre-fraction planning image 50 with the pre-procedural tracking data 20. Where the pre-procedural tracking data 20 is used, the registration and synchronization of the pre-fraction planning image 50 with the pre-procedural tracking data 20 can use the known synchronization between the pre-procedural planning data 14 and the pre-procedural tracking data 20.

For example, the pre-fraction planning image 50 is registered to the pre-procedural planning image 14, or vice versa, using the registration module 30. This synchronizes the pre-fraction planning image 50 and the pre-procedural planning image 14, whereby the synchronization between the pre-procedural tracking data 20 and the pre-fraction tracking data 50 can also be determined. In some embodiments, the segmentations in the pre-fraction and pre-procedural images 14, 50 can be used to perform registration. As another example, synchronization between the pre-procedural tracking data 20 and the pre-fraction planning image of the first treatment fraction are determined as described above. Thereafter, pre-fraction planning images of subsequent treatment fractions of the treatment plan 36 are synchronized with the pre-fraction planning image of the first treatment fraction, whereby the synchronization between the pre-procedural tracking data 20 and the pre-fraction tracking data of the subsequent treatment fractions can also be determined.

The therapy delivery apparatus 46, such as a LINAC, delivers therapy, such as ablation therapy, to the patient 14. The therapy typically includes radiation, such as one or more of x-rays, protons, high-intensity focused ultrasound (HIFU), and the like. The therapy delivery apparatus 46 is controlled by a delivery control system 56 of the therapy system 10 in accordance with the treatment plan 36 and the correspondences 38.

During therapy delivery, the delivery control system 56 receives real-time tracking data 58 from the delivery tracking system 54. The real-time tracking data 58 includes the external body surface of the pre-fraction planning 50 and pre-procedural planning image 14. When the treatment plan 36 includes a plurality of PTVs corresponding to different motion phases (e.g., respiratory phases), the delivery control system 56 determines the current motion phase using the real-time tracking data 58 or some other external data. The parameters of the treatment plan (e.g., the PTV) are then dynamically adjusted based on the current motion phase.

In addition to using real-time tracking data 58 to determine the current motion phase, the delivery control system 56, by a body surface tracking module 60, determines the location of the target based on the real-time tracking data 58. As should be appreciated, it's well known to align the coordinate frame of the therapy delivery apparatus 46 to the coordinate frame of the treatment plan 36 prior to therapy delivery. This can be extended to align the coordinate frame of the delivery tracking system 54 to the coordinate frames shared by the treatment plan 36 and the correspondences 38.

Alignment of the coordinate frames of the therapy delivery apparatus 46, the treatment plan 36, the correspondences 38 and the real-time tracking data can be based on the known relationship between the coordinate frames of the pre-fraction imaging system 48 and the therapy delivery apparatus 46 (e.g., determined by a calibration procedure). Using the pre-fraction planning image 50 or some other image generated by the pre-fraction imaging system 48, the coordinate frame of the real-time tracking data 58 can be translated to the coordinate frame of the therapy delivery apparatus 46 by, for example, registering the real-time tracking data 58 to the pre-fraction planning image 48 and using the known relationship. Translation between the coordinate frame shared by the treatment plan 36 and the correspondences 38 and the coordinate frame of the therapy delivery apparatus 46 can also be performed by registering the planning image used to generate or update the treatment plan 36 with the pre-fraction planning image 48, or some other image generated by the pre-fraction imaging system 48, and using the known relationship.

Assuming the relationship between the coordinate frame of the real-time tracking data 58 and the therapy delivery apparatus 46 is known, the location of the target can be determined by translating the real-time tracking data 58 to the coordinate frame of the therapy delivery apparatus 46, or vice versa, and applying the correspondences 38 to the real-time tracking data 58. For example, where the correspondences 38 are distance vectors, the distances can be added or subtracted from the external body surface, as necessary. In some instances, the correspondences 38 correspond to specific motion phases. Hence, the appropriate correspondences are used for the current motion phase, determined above.

Based on the determined location of the target, the delivery control system 56 can perform delivery gating by a gate module 62. When the treatment plan 36 includes a plurality of PTVs corresponding to motion phases, the gate module 62 can gate the treatment beams based on whether the current motion phase corresponds to one of the PTVs. Additionally, the location of the one or more PTVs of the treatment plan 36 can be defined in the treatment plan 36. If the determined location of the target falls outside the current PTV, the treatment beams can be gated off until the target returns to the PTV.

Alternatively, based on the determined location of the target, the delivery control system 56 can perform dynamic PTV by a dynamic PTV module 64. Dynamic PTV refers to changing the location of the current PTV based on the determined location of the target. For example, the path of the target is followed by changing the positions of multi-leaf collimator (MLC) leaves on a linear accelerator (linac).

The planning system 22 and the delivery control system 56 include one or more program memories 66, 68 and one or more processors 70, 72. The program memories 66, 68 store processor executable instructions for carrying out the functions associated with the planning system 22 and the delivery control system 56, including those associated with the user interface module 26, the segmentation module 24, the body surface tracking modules 32, 60, the optimization module 34, the registration module 30, the synchronization module 28, the gate module 62, and the dynamic PTV module 64. The processors 70, 72 execute the processor executable instructions stored on the memories 66, 68. The planning system 22 and/or the delivery control system 56 further include one or more system buses 74, 76 facilitating communication between the processors 70, 72, the program memories 66, 68, the user input device 42, and the user output device 40.

Figure 2:
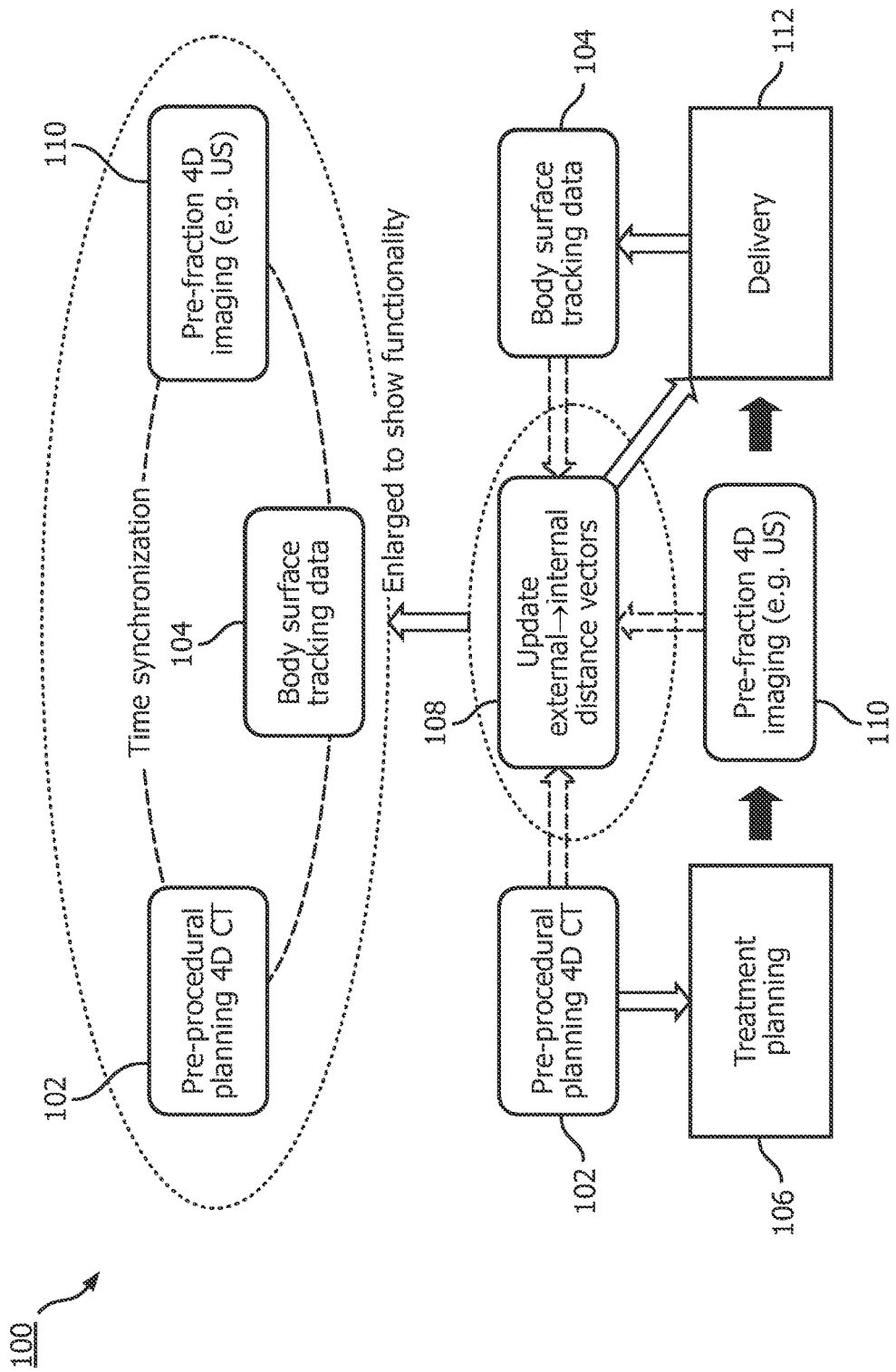
FIG. 2 illustrates an example of the workflow of the therapy system of FIG. 1.

With reference to FIG. 2, an example 100 of the workflow of the therapy system 10 of FIG. 1 is illustrated. A pre-procedural planning 4D CT image 102 is generated using, for example, the pre-procedural imaging system 12. Further, body surface tracking data 104 for the pre-procedural planning 4D CT image is generated using, for example, the pre-procedural body surface tracking system 18. The pre-procedural planning 4D CT image 102 is then used for treatment planning 106, thereby generating a treatment plan. Further, the pre-procedural planning 4D CT image 102 is used in conjunction with the body surface tracking data 104 to generate 108 distance vectors spanning from an external body surface of the patient 16 to the internal surface of the target of the patient 16. The external body surface is determined from the body surface tracking data 104, and the internal target surface is determined from the pre-procedural 4D CT image 102.

Before select treatment fractions, pre-fraction planning images 110, such as 4D US images, are generated using, for example, the pre-fraction imaging system 48. Further, body surface tracking data 104 for the pre-fraction planning images 110 is generated using, for example, the pre-fraction body surface tracking system 54. The pre-fraction planning images 110 are then used to update the treatment plan before corresponding treatment fractions (e.g., to account for a smaller target and PTV due to shrinkage from the earlier fractions). For example, the updating includes registering and transforming of the pre-procedural planning 4D CT image 14 into the pre-fraction 4D US image 50 to adjust the target, OARs and other anatomy for the changes in size, shape and relationship due to the treatment in the proceeding fractions. Further, the pre-fraction planning images 110 are used in conjunction with the body surface tracking data 104 to update 108 distance vectors spanning from the external body surface of the patient 16 to the internal surface of the target of the patient 16. As should be appreciated, the pre-procedural planning 4D CT 102, the body surface tracking data 104 and the pre-fraction planning images 110 are temporally synchronized, for example, based on motion phase, such as respiratory phase.

At the scheduled time for a treatment fraction, and after updating the treatment plan and/or the distance vectors for the treatment fraction, if the updated plan and correspondences are available, the patient undergoes therapy delivery 112 using, for example, the therapy delivery apparatus 46. Therapy is delivered using adaptive paradigms, such as gating and dynamic PTV, based on the treatment plan, the distance vectors, and real-time body surface tracking data 104.

Figure 3:
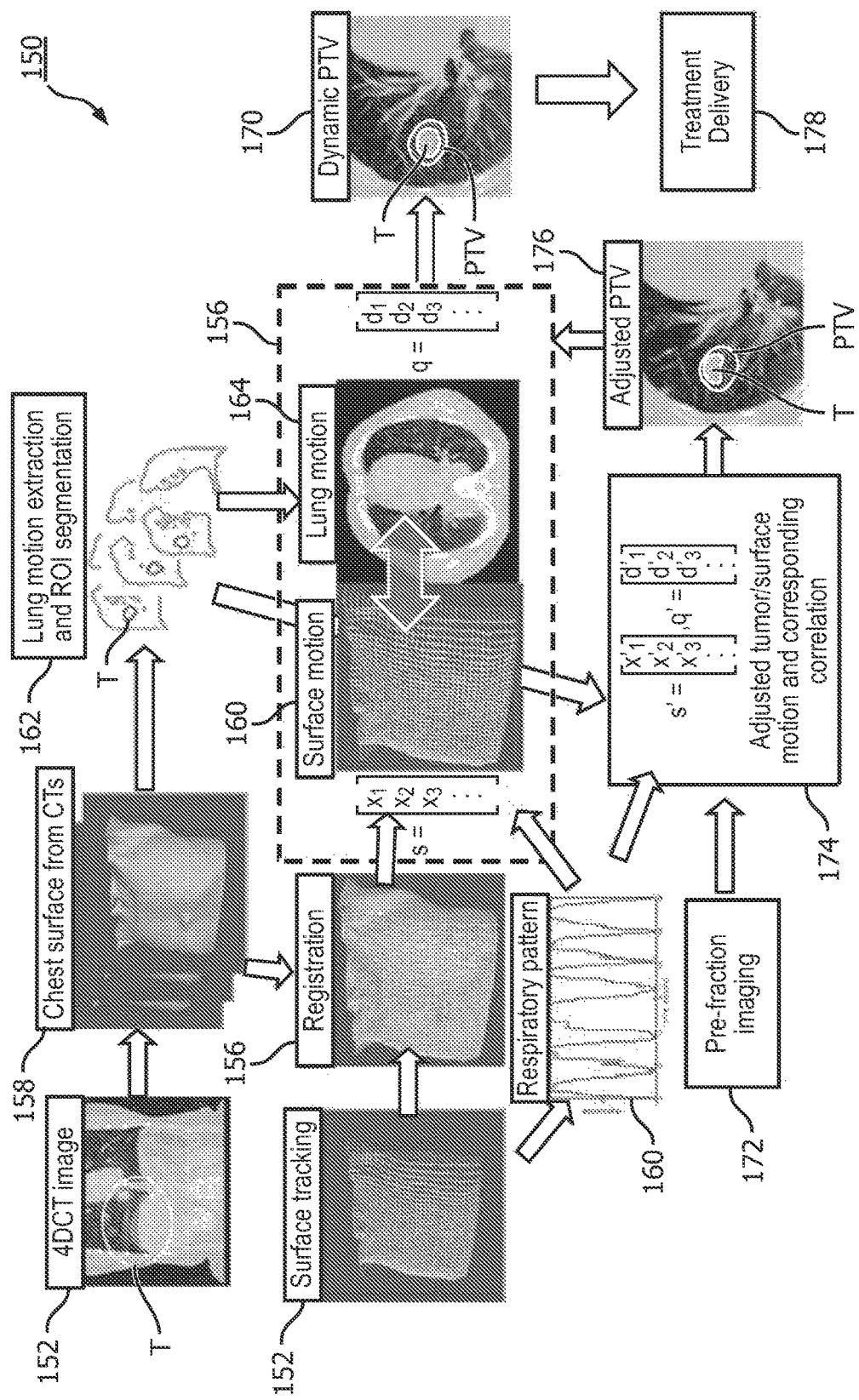
FIG. 3 illustrates another, more detailed example of the workflow of the therapy system of FIG. 1.

With reference to FIG. 3, another, more detailed example 150 of the workflow of the therapy system 10 of FIG. 1 is illustrated. A pre-procedural planning 4D CT image 152 including a target T within a lung, surrounding normal tissue, and an external chest surface of a patient is generated. Further, tracking data 154 of the external chest surface is generated. The tracking data 154 is then registered 156 to the external chest surface 158 of the pre-procedural planning 4D CT image 152, and used to identify the respiratory pattern 160 of the patient. Further, the pre-procedural planning 4D CT image 152 is segmented 162 to delineate ROIs, such as the target.

Based on the delineations, a lung and target motion model 164 is determined, which is represented by a vector q. Further, based on the registered surface tracking data, a surface motion model 166 of the external chest surface is determined, which is represented by a vector S. Based on the motion models 164, 166 and the respiratory phase, a distances vector between the external chest surface and the target is determined 168, for example, by taking the difference of the q and S. Further, based on the motion models 164, 166 and the respiratory phase, a treatment plan with a dynamic PTV 170 is determined 168. The PTV is denoted by the generally oval line surrounding and slightly spaced from the target T.

Before select treatment fractions, pre-fraction 4D images 172, such as 4D MR images, are generated. The pre-fraction 4D images 172 include the target, the surrounding normal tissue of the target, and typically the external chest surface of a patient. Further, additional tracking data 154 of the external chest surface is generated. The pre-fraction 4D images 172 and the additional tracking data 154 are then used to update 174 the lung and target motion model 164, which is represented by a vector q', and the surface motion model 166, which is represented by a vector S'. These updated models, in turn, are used to adjust 176 the dynamic PTV 170. Note that the target and PTV have shrunk from an almost circular shape in the original or an earlier PTV 170 to a smaller more kidney shape in the adjusted PTV 176.

At the scheduled time for a treatment fraction, and after updating the treatment plan and/or the distance vectors for the treatment fraction, if the updated plan and correspondences are available, the patient undergoes therapy delivery 178. Therapy is delivered using adaptive paradigms, such as gating and dynamic PTV, based on the treatment plan, the distance vectors, and real-time tracking data 154.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a controller includes at least one memory and at least one processor, the processor executing processor executable instructions on the memory; a user input device includes one or more of a mouse, a keyboard, a touch screen display, one or more buttons, one or more switches, one or more toggles, and the like; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A therapy planning system for treating an internal target of a patient using a therapy delivery control system configured to deliver therapy to the patient, said therapy planning system comprising:
   at least one processor programmed to:
      receive a treatment plan to treat the internal target, the treatment plan including a plurality of treatment fractions including correspondences between the internal target and an external body surface based on (i) a pre-procedural planning image which is segmented to delineate the internal target, and (ii) pre-procedural tracking data;
      before delivery of one or more selected treatment fractions of the plurality of treatment fractions:
         receive a pre-fraction planning image of the target;

segment the internal target in the pre-fraction planning image by registering the pre-fraction planning image to the segmented pre-procedural planning image;

receive tracking data of the external body surface of the patient; and update the correspondences between the internal target and the external body surface based on (i) the segmented pre-fraction planning image and (ii) the received tracking data of the external body surface of the patient; and provide the treatment plan and the updated correspondences to the therapy delivery control system in accordance with the treatment plan and using the updated correspondences.

2. A therapy system for treating an internal target of a patient using a therapy delivery control system configured to deliver therapy to the patient, said therapy system comprising:

at least one processor programmed to after one or more of a plurality of treatment fractions:

receive a treatment plan to treat the internal target, the treatment plan including the plurality of treatment fractions including correspondences between the internal target and an external body surface based on (i) a pre-procedural planning image which is segmented to delineate the internal target, and (ii) pre-procedural tracking data, wherein a size and shape of the internal target change with the delivery of therapy during the plurality of treatment fractions;

before delivery of one or more selected treatment fractions of the plurality of treatment fractions:

receive a pre-fraction planning image of the target;

segment the internal target in the received pre-fraction planning image and registering the received pre-fraction planning image to the segmented pre-procedural planning image;

receive tracking data of the external body surface of the patient;

update the size and the shape of the internal target and the correspondences between the internal target with the updated size and shape and the external body surface based on the segmented pre-fraction planning image and the received tracking data;

update the treatment plan based on the updated size and shape of the internal target from the segmented pre-fraction planning image and the updated correspondence between the internal target and the external body surface; and provide the updated treatment plan and the updated correspondences to the therapy delivery control system to control delivery of the therapy in accordance with the updated treatment plan and using the updated correspondences.

3. The therapy planning system according to claim 1, wherein the treatment plan is generated using a pre-procedural planning image including the target, and wherein the received tracking data corresponds to the generation of the pre-procedural planning image.

4. The therapy planning system according to claim 1, wherein the pre-fraction planning image is four-dimensional (4D).

5. The therapy planning system according to claim 1, wherein the therapy delivery control system is further configured to:

dynamically adjust a planning target volume (PTV) of the treatment plan using the updated correspondences during delivery of the therapy.

6. The therapy planning system according to claim 1, wherein the therapy delivery control system is further configured to:

gate a therapy beam using the updated correspondences during delivery of the therapy.

7. The therapy planning system according to claim 1, wherein the at least one processor is further programmed to:

temporally synchronize the segmented pre-fraction planning image with the received tracking data.

8. The therapy planning system according to claim 7, wherein the temporal synchronization is based on respiratory phases of the patient.

9. The therapy planning system according to claim 1, wherein the treatment plan is generated using the segmented pre-procedural planning image which includes the target, and wherein the at least one processor is further programmed to:

temporally synchronize the segmented pre-procedural planning image with the segmented pre-fraction planning image.

10. A therapy delivery method for treating an internal target of a patient using a therapy delivery control system configured to deliver therapy to the patient, said therapy delivery method comprising:

after one or more of a plurality of treatment fractions:

receiving a treatment plan to treat the internal target, the treatment plan including the plurality of treatment fractions including correspondences between the internal target and an external body surface based on (i) a pre-procedural planning image which is segmented to delineate the internal target, and (ii) pre-procedural tracking data, wherein a size and shape of the internal target change with the delivery of therapy during the plurality of treatment fractions;

before delivery of one or more selected treatment fractions of the plurality of treatment fractions:

receiving a pre-fraction planning image of the target;

segmenting the internal target in the received pre-fraction planning image and registering the received pre-fraction planning image to the segmented pre-procedural planning image;

receiving tracking data of the external body surface of the patient;

updating the size and the shape of the internal target and the correspondences between the internal target with the updated size and shape and the external body surface based on the segmented pre-fraction planning image and the received tracking data;

updating the treatment plan based on the updated size and shape of the internal target from the received segmented pre-fraction planning image and the updated correspondence between the internal target and the external body surface; and providing the updated treatment plan and the updated correspondences to the therapy delivery control system to control delivery of the therapy in accordance with the updated treatment plan and using the updated correspondences.

11. The therapy delivery method according to claim 10, wherein the treatment plan is generated using a pre-procedural planning image of the target, and wherein the received tracking data corresponds to the generation of the pre-procedural planning image.

12. The therapy delivery method according to claim 10, wherein the pre-fraction planning image is four-dimensional (4D).

13. The therapy delivery method according to claim 10, further including:
dynamically adjusting a planning target volume (PTV) of the treatment plan using the updated correspondences during delivery of the therapy.

14. The therapy delivery method according to claim 10, further including:
gating a therapy beam using the updated correspondences during delivery of the therapy.

15. The therapy delivery method according to claim 10, further including:
temporally synchronizing the received pre-fraction planning image with the received tracking data.

16. The therapy delivery method according to claim 15, wherein the temporal synchronization is based on respiratory phase of the patient.

17. One or more processors programmed to perform the therapy delivery method according to claim 10.

18. A non-transitory computer readable medium carrying software which controls one or more processors of a therapy system for treating an internal target of a patient using a therapy delivery control system configured to deliver therapy to the patient, the one or more processors being programmed to after one or more of a plurality of treatment fractions:
receive a treatment plan to treat the internal target, the treatment plan including the plurality of treatment fractions including correspondences between the internal target and an external body surface based on (i) a pre-procedural planning image which is segmented to delineate the internal target, and (ii) pre-procedural tracking data, wherein a size and shape of the internal target change with the delivery of therapy during the plurality of treatment fractions;
before delivery of one or more selected treatment fractions of the plurality of treatment fractions:
receive a pre-fraction planning image of the target;
segment the internal target in the received pre-fraction planning image and registering the received pre-fraction planning image to the segmented pre-procedural planning image;
receive tracking data of the external body surface of the patient;
update the size and the shape of the internal target and the correspondences between the internal target with the updated size and shape and the external body surface based on the segmented pre-fraction planning image and the received tracking data;
update the treatment plan based on the updated size and shape of the internal target from the segmented pre-fraction planning image and the updated correspondence between the internal target and the external body surface; and
provide the updated treatment plan and the updated correspondences to the therapy delivery control system to control delivery of the therapy in accordance with the updated treatment plan and using the updated correspondences.

* * * * *